United States Patent [19]

Maini

[11] Patent Number: 4,747,848

[45] Date of Patent: May 31, 1988

[54] VASCULAR GRAFTS

[75] Inventor: Roshan Maini, Bridge of Weir, Scotland

[73] Assignee: Vascutek Limited, Ayr, Scotland

[21] Appl. No.: 788,718

[22] Filed: Oct. 17, 1985

[30] Foreign Application Priority Data

Nov. 30, 1984 [GB] United Kingdom ............... 8430265

[51] Int. Cl.$^4$ .............................................. A61F 2/06
[52] U.S. Cl. ......................................... 623/1; 623/66; 530/354
[58] Field of Search .................. 128/334 R; 623/1, 2, 623/11, 66, 15; 260/117, 121; 426/576; 523/112, 105; 530/354

[56] References Cited

U.S. PATENT DOCUMENTS 3,106,483 10/1963 Kline ....................................... 623/1
4,167,045 9/1979 Sawyer .................................. 623/1
4,654,464 3/1987 Mittelmeier et al. ................ 623/16

OTHER PUBLICATIONS

Dorland, *The American Illustrated Medical Dictionary*, Saunders Co., 1923, pp. 52, 458.

*Primary Examiner*—Richard J. Apley
*Assistant Examiner*—Alan W. Cannon
*Attorney, Agent, or Firm*—Larson and Taylor

[57] ABSTRACT

A method of producing a vascular graft comprises impregnating a tube of flexible porous material with gelatinous material which contains a gelatin with has been treated to cause it to contain a predetermined number of amino groups less than that normally present in untreated gelatin then treating the impregnated tube to cause the amino groups to form cross links with one another. The gelatin may be treated by reacting it with the anhydride or the chloride of a polycarboxylic acid.

7 Claims, No Drawings

VASCULAR GRAFTS

This invention relates to artificial vascular grafts used to take the place of at least sections of blood vessels in human and animal bodies. It is an object of the present invention to provide a vascular graft which has important advantages over known artificial grafts.

Artificial grafts must have or acquire some degree of permeability after implantation so that tissue ingrowth can take place. The commercially acceptable manufacturing processes usually employed at present produce grafts which while meeting satisfactorily the other necessary characteristics have such a high degree of porosity that the seepage of blood through the grafts initially at least is unacceptably high.

To reduce this initial high rate of seepage of blood it has been the custom to impregnate grafts prior to implantation with blood usually obtained from the prospective recipient. This operation has the effect of causing enough pre-clotting of blood on the graft to reduce the initial escape of blood through the wall of the graft to an acceptable level while leaving the permeability sufficient to allow the commencement and continuation of tissue growth into the grafts.

With the described method of pre-impregnation there is still present the difficulty that pre-impregnation is time-consuming, it requires the use of some of the blood of the prospective recipient and there is little or no control over the rate of the necessary break down of the fibrin in the impregnating blood. There is also an added difficulty where the prospective recipient suffers from a blood coagulation defect.

Attempts have been made to produce grafts which can be implanted in a substantially impermeable dry state and which immediately after implantation begin to become permeable. Such proposals have taken the form of impregnating porous tubular structures with such materials as gelatin, collagen or albumin. A gelatin impregnated graft is not porous but when exposed to water the gelatin degrades by hydrolysis the rate at which hydrolysis proceeds being higher at the body temperature of 372° C. than it is at normal temperature. As such grafts normally become progressively more porous at a rate too fast to keep pace with clotting and tissue growth it has been proposed to treat the gelatin in such a way as to cause cross links to form between the amino groups present in the gelatin molecules. Such cross linking renders the gelatin more resistant to hydrolysis and thus reduces considerably the rate at which the permeability of the graft increases. One method of initiating cross linking comprises exposing the gelatin to formaldehyde. The difficulty here is in controlling the number of cross links formed and thus the rate of increase of porosity and heretofore there has been no sure method of providing a graft which would become progressively more porous at a predetermined rate. All that could be done was to expose the gelatin to the cross linking agent for a time believed to provide the desired amount of cross linking and then to remove the cross linking agent. The known method is actually an art rather than a science and the behaviour of the grafts produced is unpredictable and inconsistent.

The present invention has for its object to provide a graft which requires no pre-impregnation with blood and which after implantation starts to degrade and become permeable at an accurately known rate. It is to be understood that according to the medical circumstances of different implantations the porosity of the implanted grafts should increase at a rate only sufficient to avoid haemorrhage occurring. The process of the invention permits such a degree of control of the rate of porosity increase.

A method of producing a vascular graft according to the invention by impregnating a tube of flexible porous material with gelatinous material then treating the impregnated tube to cause only the amino groups always present in the molecules of gelatinous material to form cross links is characterized by including in the gelatinous material a gelatin which has been treated to cause it to contain a predetermined number of amino groups less than that normally present in untreated gelatin.

It is an easy matter to ascertain the number of amino groups present in any particular sample of gelatin the other main ionic groups being hydroxyl, carboxyl and arginine groups. However it may be said here that the number of amino groups present in untreated gelatin normally constitutes around 3.5% of all groups present, see The Science and Technology of Gelatin published by Academic Press, 1977, particularly page 94.

For manufacturing reasons it is sometimes convenient to have all the treated gelatin intended to be used for grafts with different porosity characteristics treated to the same extent, for example 75%, i.e. 75% of all the amino groups originally present are converted to other groups, the rate of porosity change being then controlled by mixing the treated gelatin containing the known proportion of converted amino groups with a gelatin not so treated in a predetermined proportion.

The treatment to reduce the number of amino groups only in a gelatin may comprise reacting the gelatin with the anhydride or the chloride of a polycarboxylic acid. A suitable polycarboxylic acid is succinic acid $COOHCH_2CH_2COOH$. The treatment is accurately controllable so that it is possible to produce a treated gelatin in which a predetermined proportion of the amino groups originally occurring in the gelatin has been converted to groups of other types. An example of a gelatin mixture found to be satisfactory in particular circumstances contains a gelatin treated to convert 75% of the amino groups to carboxyl groups.

A plasticizing agent may be included in the mixture of treated and untreated gelatin.

Materials capable of causing the formation of cross links between the amino groups only in a gelatin are aldehydes such as formaldehyde or gluteraldehyde or a mixture of formaldehyde and gluteraldehyde in predetermined proportions. The cross linking treatment may be a two part treatment in which the impregnated graft is treated first with formaldehyde and then with gluteraldehyde.

As a final step the graft may be sterilized purely as an additional precaution. Such a sterilizing step is not strictly speaking necessary since the formaldehyde treatment is a sterilizing treatment in itself.

The treatment causes at least some of the amino groups on each gelatin molecule to be converted to other groups on the gelatin molecule, particularly hydroxyl and carboxyl groups. Since the treatment can be performed to provide accurately known proportions of amino and other groups on each molecule of gelatin and the proportion of other groups to amino groups is known within close limits in ordinary untreated gelatin, by treating the impregnating gelatin to a predetermined percentage of amino group conversion or choosing particular proportions for a mixture containing gelatin treated to a known percentage amino group conversion and untreated gelatin it is possible to know exactly how many amino groups are present in relation to the other groups. Since it is only the amino groups which become cross linked the degree of cross linking can be accurately determined since when the gelatin mixture is exposed to the cross linking medium, irrespective of how long such exposure takes place cross linking can only take place up to the extent of the number of amino groups present since the other groups will not cross link. It is the number of cross links which determines the rate at which degradation of the gelatin takes place because it is through the breaking of the cross links that the gelatin becomes permeable. In the cross linking operation the amino groups which cross link form cross links with other amino groups on the same molecule and on other molecules whether of treated or untreated gelatin.

When the graft is implanted the aqueous constituent of the recipient's blood causes hydrolysis of the gelatin mixture to start, causing the gelatin to swell giving increased access of the water to the cross links which start to rupture under the hydrolizing action. A low degree of cross linking resulting from a high percentage of amino group conversion provides a high degree of swelling and quicker rupture under the hydrolizing action whereas a high degree of cross linking causes less swelling and a smaller rate of rupture of the cross links. Thus the time taken for the cross links to be destroyed is readily predetermined according to the percentage of amino group conversion whether using only a treated gelatin alone or a mixture of a treated gelatin and an untreated gelatin.

Further control of the rate of degradation can be effected by the proportion of formaldehyde or gluteraldehyde used in the cross linking treatment. Cross links formed by the action of formaldehyde are more readily broken than those formed by gluteraldehyde. A high proportion of gluteraldehyde to formaldehyde used in the treatment process provides a graft in which degradation starts to take place a comparatively long time after implantation of the graft.

The control of the rate of degradation also provides an improved effect in gelatin coatings intended to promote other biological actions. It is known that gelatin contains binding sites for fibronectins. Fibronectin is a protein associated with the adhesion of cells to substrates and collagen-based materials have been used for example as burn dressings to encourage the adhesion and growth of epithelial cells.

EXAMPLE 1

A tube formed as a knitted structure of textile material was impregnated under vacuum with a mixture of a gelatin which had been treated with the chloride of succinic acid to cause 75% of the amino groups present to be converted to other groups and a normal gelatin not so treated in the proportion 50% treated to 50% untreated gelatin, the temperature at which impregnation took place was 65° C. The gelatin mixture was allowed to gel and the tube was then subjected to a treatment with a 20% solution of formaldehyde at pH4 and 4° C. for a period of 16 hours.

The formed vascular graft was then washed in five changes of pyrogen-free water at room temperature.

A graft produced according to the example described became fully porous in 25–30 hours under laboratory test conditions.

EXAMPLE 2

A graft was prepared as described in Example 1 except that 75% treated gelatin, i.e. gelatin which had 75% of its amino groups converted to other groups, was used without admixture with untreated gelatin. This graft became fully porous in 5–8 hours under laboratory test conditions.

For purposes of comparison grafts were prepared using untreated gelatin only and these were found to become fully porous in a time exceeding 45 hours under the same laboratory test conditions.

What I claim is:

1. A method of producing a vascular graft which after implantation becomes permeable at a predictable rate comprising ascertaining the proportion of amino groups present in a particular sample of untreated gelatin, treating a first quantity of gelatin taken from said sample to cause a predetermined proportion of the amino groups in said first quantity of gelatin to be converted to other groups whereby to cause the proportion of amino groups present in said first quantity of gelatin to be reduced to a predetermined proportion, mixing a further quantity of untreated gelatin taken from said sample and a quantity of said treated gelatin in a predetermined proportion to produce a gelatinous mixture having a predetermined proportion of amino groups, impregnating a tube of flexible porous material with said gelatinous mixture, and treating the impregnated tube to cause the amino groups present in the gelatinous mixture to form cross links with one another.

2. A method of producing a vascular graft as claimed in claim 1 in which the treated gelatin is treated by reacting it with the anhydride or the chloride of a polycarboxylic acid.

3. A method of producing a vascular graft as claimed in claim 2 in which the polycarboxylic acid comprises succinic acid COOHCH$_2$CH$_2$COOH.

4. A method of producing a vascular graft as claimed in claim 1 in which said first quantity of gelatin is treated to cause 75% of the amino groups originally in the gelatin before treatment to be converted to carboxyl groups.

5. A method of producing a vascular graft as claimed in claim 1 in which the gelatinous material is treated with at least one aldehyde to cause the formation of cross links in the amino groups.

6. A method of producing a vascular graft as claimed in claim 5 in which the cross linking treatment is a two part treatment comprising treating the impregnated tube first with formaldehyde and then with gluteraldehyde.

7. A vascular graft produced by the process of claim 1.

* * * * *